US007833801B2

(12) United States Patent
Stasiak et al.

(10) Patent No.: US 7,833,801 B2
(45) Date of Patent: Nov. 16, 2010

(54) FREE-STANDING NANOWIRE METHOD FOR DETECTING AN ANALYTE IN A FLUID

(75) Inventors: James Stasiak, Corvallis, OR (US); Paul H. McClelland, Monmouth, OR (US); David E. Hackleman, Monmouth, OR (US); Grant Pease, Corvallis, OR (US); R. Stanley Williams, Palo Alto, CA (US); Kevin Peters, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 1032 days.

(21) Appl. No.: 11/601,062

(22) Filed: Nov. 17, 2006

(65) Prior Publication Data

US 2008/0204048 A1    Aug. 28, 2008

Related U.S. Application Data

(62) Division of application No. 10/309,608, filed on Dec. 3, 2002, now Pat. No. 7,163,659.

(51) Int. Cl.
*G01N 33/00* (2006.01)
(52) U.S. Cl. .................. 436/149; 422/68.1; 422/99
(58) Field of Classification Search ............ 422/68.1, 422/99; 436/149
See application file for complete search history.

(56) References Cited

U.S. PATENT DOCUMENTS 6,399,177 B1   6/2002 Fonash et al.
6,958,216 B2   10/2005 Kelley et al.
7,129,554 B2   10/2006 Lieber et al.

FOREIGN PATENT DOCUMENTS

EP          0244326       11/1987
WO     WO 02/081372      10/2002

OTHER PUBLICATIONS

A.J. Yin, et al., Fabrication of Highly Ordered Metallic Nanowire Arrays by Electrodeposition, Applied Physics, vol. 79, Aug. 2001.
Berggren, et al., Capacitive Biosensors, Electroanalysis, V. 13(3), 2001, pp. 173-180.

(Continued)

*Primary Examiner*—Sam Siefke

(57) ABSTRACT

A sensor device and method for detecting the presence of an analyte in a fluid solution are disclosed. The sensor device system can comprise a substrate and an array of free-standing nanowires attached to the substrate. The array can include individual free-standing nanowires wherein each of the individual free-standing nanowires have a first end and a second end. The first end can, in some embodiments, be attached to the substrate and the second end unattached to the substrate. Such individual free-standing nanowires are configured for electrical communication with other individual free-standing nanowires through the first end. A chip or computer can be electrically coupled to the array of free-standing nanowires for receiving electrical information from the array of free-standing nanowires. In some embodiments a power source can be used to send current through the nanowire array.

11 Claims, 3 Drawing Sheets

OTHER PUBLICATIONS

M. Klein, et al, Monitoring of Antibody-Antigen Reactions with Affinity Sensors: Experiments and Models, Sensors and Actuators B 26-27 (1995) pp. 474-476.

Varlan, et al, Capacitive Sensor for the Allatostatin Direct Immunoassay, Sensors and Actuators B 44 (1997) 334-340.

Yi Cui, et al, Nanowire Nanosensors for Highly Sensitive and Selective Detection of Biological and Chemical Species, Science, vol. 293, Aug. 2001.

T. I. Kamins, et al, Chemical Vapor Deposition of Si Nanowires Nucleated by $TiSi_2$ Islands on Si, Applied Physics, vol. 76, No. 5, Jan. 2000.

Wei Zhang, et al, Multilevel Nanoimprint Lithography with Submicron Alignment over 4 in. Si Wafers, Applied Physics, vol. 79, No. 6, Aug. 2001.

FREE-STANDING NANOWIRE METHOD FOR DETECTING AN ANALYTE IN A FLUID

The present application is a divisional of U.S. patent application Ser. No. 10/309,608, filed Dec. 3, 2002, now U.S. Pat. No. 7,163,659 which is hereby incorporated by reference.

FIELD OF THE INVENTION

The present invention relates generally to chemical and biological analysis. More particularly, the present invention relates to free-standing nanowire sensors.

BACKGROUND OF THE INVENTION

Chemical analysis and the identification of biological materials has long been the domain of analytical biology, chemistry and physics. The methods used often require cumbersome laboratory instrumentation in a centralized laboratory and long sampling and analysis times. However, over the last few decades, the increasing awareness and concern regarding factors that influence health, safety, appliance performance, and the environment has created a demand for user-friendly technologies capable of detecting, identifying, and monitoring chemical, biological, and environmental conditions in real-time. In response to these needs, a successful commercial market focused on exploiting, simplifying, improving, and cost-reducing sophisticated laboratory procedures and hardware has emerged. Home $CO_2$ monitors, drinking water purity monitors, and smoke detectors are now very common. Many of these devices have become requirements in new homes and workplaces. In addition to the environmental sensor products, there is a rapidly growing market focused on personal health monitors and health screening appliances. For example, there are a number of systems on the market today that provide sampling and analysis of blood for glucose monitoring. Analogous to the computing revolution, the evolution from centralized sensing to distributed and embedded sensing is well underway. Given these trends, it is safe to predict that intelligent, portable, wireless, web-enabled, self-diagnostic appliances exploiting a broad range of chemical and biosensor technology will be in demand in the near future.

An important, competing technology is chemically sensitive field effect transistors (ChemFETs). ChemFETs rely on chemically initiated electric field fluctuations above the two dimensional FET channel to modify the source-drain conductance. While ChemFETs exploit the same physical principles for detection as nanowires, they require large planar surface areas over the FET channel and lack the extreme sensitivity and discrimination enabled by the high surface-to-volume ratios of nanowires.

Other proposed detection schemes based on nanowires require that good electrical contacts be made to both ends on each nanowire that is used in a detector. Disadvantages of this approach include the requirement of placing and contacting individual nanowires which is expensive and time consuming, and that the yield of such devices with good electrical contacts may be low. Devices that are based on a single nanowire are also not very sensitive and can provide spurious signals.

In each of the applications above and with others, there is and will be an ever-increasing demand for lower detection limits, higher selectivity and sensitivity, portability and real-time response. Although substantial improvements in detector sensitivity and response have been achieved by leveraging advances in microelectronic, micromechanical, and microfluidic technologies, in order to meet the demands for real-time, single-molecule discrimination, continued and innovative improvements will be required. It is likely that these improvements will require the development of new technologies.

SUMMARY OF THE INVENTION

It has been recognized that it would be advantageous to develop a chemical or biological sensor that is much more sensitive than the standard sensors available today.

The invention provides a sensor device comprising a substrate and an array of free-standing nanowires. The array comprises individual free-standing nanowires, each of which has a first end and a second end. The first end is typically attached to the substrate and the second end is unattached to the substrate, thereby providing a free-standing configuration. This does not require that all free-standing nanowires be attached to the substrate in this manner. For example, some nanowires may be attached to the substrate at a single end, and others can be present as part of an amorphous jumble of nanowires. Thus, many of such nanowires can actually lack any direct contact to the substrate, and yet are configured for electrical communication with the substrate and one another via random contact points with other nanowires, and also via a capacitive effect between nanowires. Such a nanowire "fuzz" would can be positively planted or placed onto the substrate rather than formed through in situ deposition or growing.

The individual free-standing nanowires are configured for electrical communication with other individual free-standing nanowires through the first end. This can be either through a substrate to which it is attached, or a coating on the substrate, either of which (or both of which) can be semi-conductive or conductive. For example, the substrate may not be conductive in some cases, e.g., polymer or glass substrates. In these circumstances, a conductive or semi-conductive material can be deposited to the non-conductive substrate. In other embodiments, the substrate will be conducive or semi-conductive and no secondary coating will be present. In still another embodiment, both a conducting or semi-conducting substrate and coating can be present. In any of these embodiments, examples of compositions that can be used include silicon, germanium, silver, gold, zinc oxide, gallium arsenide, tin oxide, cadmium sulfide, radmium telluride, cadmium selenide, and combinations thereof. These are examples of conducting and/or semiconducting layers. To the substrate or the applied layer, the array of free-standing nanowires can be grown on the substrate, or positively planted. Methods such as chemical vapor deposition can be used when growing the nanowires, though any other technique known to those skilled in the art can be used.

A device for signal measurement, such as a chip or computer, is also typically electrically coupled to the array of free-standing nanowires for receiving electrical information from the array of free-standing nanowires. In some embodiments, current or other energy can be applied to the nanowires via a power source.

Once grown, or as part of the growing process, the array of free-standing nanowires can be functionalized with a composition that is interactive with a predetermined analyte. For example, functionalization can be by chemical attachment of a receptor or an oxidizing or reducing agent. Alternatively, functionalization can be by deposition of a desired material onto the surface of the nanowires. In one embodiment, the deposited composition can be a dielectric coating. Thus, when an individual nanowire comes in contact with an analyte, the analyte can stick to the dielectric coating by attraction to the nanowire (through the coating), providing a capacitive effect. Alternatively, deposited or chemically attached coatings can be configured to be chemically reactive with an analyte.

Though free-standing nanowires of any dimension can be used as is functional, it is preferred that the array of free-standing nanowires present on the substrate are at a density of from about $10^4$ to about $10^{13}$ nanowires/cm². Each individual nanowire of the array of free-standing nanowires can also be from 10 nm to 100 nm in thickness, and from 50 nm to 1,000,000 nm in length. The array of free-standing nanowires can be selected from the group consisting of metallic nanowires, semi-conducting nanowires, piezoelectric nanowires, and/or insulated nanowires. Such nanowires, in this nano-sized regime, can exhibit quantum behavior.

Various test fluids, including gases and liquids, can be tested for the presence of a predetermined analyte. These measurements can be taken using a single sensor, or by the additional use of a second sensor that provides a control or baseline reading. Additionally, the sensor device can be used as a capacitive plate in a capacitive system. Such an embodiment can include the array of free-standing nanowires attached to the substrate as a capacitive plate, wherein the device further comprises an opposing capacitive plate positioned in proximity to the first capacitive plate to form a capacitive system. With such a system, upon application of a current, the capacitive system can be configured for electrical communication between the first capacitive plate and the second capacitive plate in the presence of a fluid environment. To obtain a comparative measurement, a second capacitive system can be provided that is substantially the same as the capacitive system. With this arrangement, the second capacitive system can also be electrically coupled to the chip or computer wherein differential measurements comparing the capacitive system to the second capacitive system are obtainable. In further detail, in one embodiment, the counter capacitive plate can be substantially the same configuration as the array of free-standing nanowires attached to the substrate.

In an alternative embodiment, the sensor device can comprise a second substrate and a second array of free-standing nanowires configured substantially the same as the substrate and the array of free-standing nanowires, respectively, wherein the second array is also electrically coupled to the chip, computer, or other signal measurement apparatus. With this arrangement, a differential measurement comparing conductance of the array and the second array is obtainable.

In further detail, a substantially sealed chamber surrounding the second array and the second substrate (of either of the above systems) can be used. In one embodiment, the sealed chamber can be filled with a predetermined fluid atmosphere, e.g., a gas atmosphere, providing a control system. Further, the sensor device can be substantially surrounded by an outer shell that electrically and environmentally shields the array.

In accordance with a more detailed aspect of the present invention, a method of detecting the presence of an analyte in a test fluid environment can include the steps of (a) providing a first array of free-standing nanowires that is interactive with an analyte, wherein the first array of free-standing nanowires have individual nanowires that are electrically interactive with one another, and wherein the first array of free-standing nanowires is electrically coupled to a chip or computer that is human- or machine-readable; (b) exposing the first array of free-standing nanowires to a test fluid environment suspected of containing the analyte; and (c) measuring an electrical property provided by the first array of free-standing nanowires upon exposure to the test fluid environment. Additional steps can include (d) providing a second array of free-standing nanowires, wherein the second array of free-standing nanowires have individual nanowires that are electrically interactive with one another, and wherein the second array of free-standing nanowires are electrically coupled to the chip or computer; (e) exposing the second array of free-standing nanowires to a control fluid environment; and (f) comparing the electrical property provided by the second array of free-standing nanowires upon exposure to a control fluid environment to the electrical property provided by the first array of free-standing nanowires, thereby providing a differential measurement.

With respect to the above method, the second array of free-standing nanowires can also be configured to be interactive with the analyte. Additionally, if the control fluid environment is known to be void of the analyte, a basis for the comparing step can be provided. Alternatively, the second array of free-standing nanowires can be configured to be non-interactive with the analyte. Thus, if the control fluid environment and fluid environment are substantially the same fluid composition, a basis for the comparing step can be provided.

As with the previous embodiment, the first array of free-standing nanowires can be native, or functionalized with a composition interactive with the analyte. In one embodiment, the first array of free-standing nanowires can be functionalized with an insulating composition. In such a case, a capacitive electrical reading can be taken. In other embodiments, a conductive electrical reading can be taken in the presence of an analyte-containing fluid.

In another embodiment, a method of detecting the presence of an analyte in a fluid environment can comprise several steps. Such steps include (a) providing a detecting system comprising (i) a first capacitive plate having a first array of free-standing nanowires that is interactive with an analyte, wherein the first array of free-standing nanowires comprises individual nanowires that are electrically interactive with one another, and (ii) a second capacitive plate positioned in proximity to the first capacitive plate such that electrical communication between the first capacitive plate and the second capacitive plate occurs in the presence of the test fluid environment; (b) placing the test fluid environment in continuous contact with the first capacitive plate and the second capacitive plate; (c) applying electrical current to at least one of the first capacitive plate and the second capacitive plate; and (d) measuring an electrical property passed capacitively between the first capacitive plate and the second capacitive plate. This embodiment, can further comprise the steps of (e) providing a control system comprising a third capacitive plate and a fourth capacitive plate that are substantially configured the same as the first capacitive plate and the second capacitive plate, respectively, and (f) placing a control fluid that is known to be void of the analyte in continuous contact with third capacitive plate and the fourth capacitive plate, thereby providing a comparison basis for the measuring step. Alternatively, the method can comprise the steps of (e) providing a control system having a third capacitive plate and a fourth capacitive plate that are substantially configured the same as the first capacitive plate and the second capacitive plate, respectively, except that the nanowires of the third and fourth capacitive plates are not interactive with the analyte, and (f) placing the test fluid in contact with the control system, thereby providing a comparison basis for the measuring step.

Additional features and advantages of the invention will be apparent from the detailed description which follows, taken

DETAILED DESCRIPTION OF THE PREFERRED EMBODIMENT(S)

Figure 1:
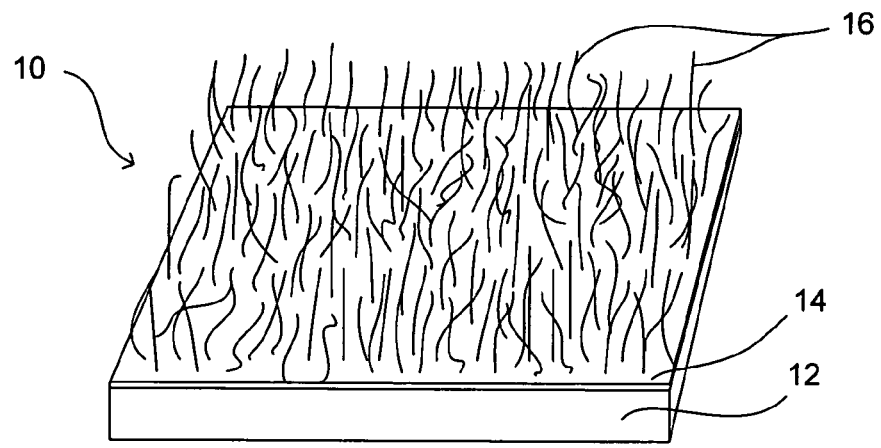
FIG. 1 is a perspective view of an array of free-standing nanowires attached through a conductive layer to a substrate in accordance with an embodiment of the present invention.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention. It is also to be understood that the terminology used herein is used for the purpose of describing particular embodiments only. The terms are not intended to be limiting.

It must be noted that, as used in this specification and the appended claims, the singular forms "a," "an," and "the" include plural referents unless the content clearly dictates otherwise.

"Free-standing nanowires" or "array of free-standing nanowires" is a forest of elongated nanowires, each having a narrow cross-section, e.g., less than 100 nm. Nanowires can be roughly equi-axial, i.e., having a small aspect ratio less than about 10 of the major and minor cross-sectional distances, and can have a larger aspect ratio (length to cross-sectional distance) that is greater than about 5. The definition of a nanowire is not meant to imply any compositional restrictions. Examples may include nanowires of gold, zinc oxide, II-VI semiconductors, and boron-doped silicon. Free-standing nanowires can also include carbon nanotubes and silicon nanowires. Additionally, the free-standing nanowires can be functionalized, such as with a composition as simple as a silicon oxide shell, or as complex as a biological receptor specifically configured to recognize a specific molecule. When growing nanowires on a substrate, the use of chemical vapor deposition on catalyst nanoparticles as a nucleation site can be used. With this method, well-controlled sizes, patterns and densities of nanowires can be grown. The substrate with attached nanowires can then be used for sensing target substances or analytes. Other methods can also be used including other growth methods, or alternatively, by methods wherein nanowires are positively planted on a substrate.

"Free-standing nanowire sensor" or "free-standing nanowire detector" can be a substrate wherein multiple nanowires are affixed at one end only, and the other end is substantially unaffixed to the substrate or other structure. The substrate can be electrically conducting or semi-conducting, and/or can be coated with a conducting or semi-conducting material. The unaffixed end (the "free standing" end) does not have a conductive pathway except back through the nanowire. Individual free-standing nanowires can incidentally contact other nanowires, as often this cannot be prevented. However, such contact will only be minimal and between substantially adjacent nanowires. The free-standing configuration eliminates the need for making two electrical connections (as is required for other nanowire based sensors and detectors) and, in some embodiments, can permit the use of "as-fabricated" nanowire arrays without requiring singulation and handling of individual nanowires.

"Analyte" shall mean a substance believed to be present in a fluid environment that is being tested for using a free-standing nanowire sensor of the present invention. The substance can be a present in a gas or a liquid, and can itself be a gas, a liquid, or a solid.

The term "interactive" when referring to the interaction between an analyte and a free-standing nanowire can include chemical reaction, physical attraction, displacement of charge, separation due to the presence of an insulating composition, or the like. In other words, interaction can be any chemical or electrical change that occurs between an analyte and a free-standing nanowire that can be detected.

Measurements can be taken in accordance with the present invention by measuring the conductance or conductance change in the array of nanowires, and/or by a capacitance measurement. When referring to "capacitance" in the context of the present invention, two basic embodiments are included. In one embodiment, an array of nanowires can act as a capacitive plate in a capacitor system. In another embodiment, an individual nanowire can act as a capacitive plate, wherein a dielectric coating on the nanowire provides space between the nanowire and an analyte.

Metallic and semiconductor nanowires can provide a sensor technology that enables highly selective, real-time electrically based detection of biological and chemical materials. The remarkable properties of these devices enable innovative products that provide real-time information regarding personal health status, environmental conditions, chemical sensing, and the like. Furthermore, laboratory-based instrumentation containing nanotechnology-enabled sensors and detectors can provide unprecedented resolution and characterization of single molecules, proteins, and/or DNA. Since the diameter of a nanowire is very small (typically less than 100 nm), the electrical conductance can be extremely sensitive to small electronic perturbations and fluctuations at or near their surfaces. Perturbations can be sensed either by capacitive systems, and/or by conductive systems.

In accordance with one aspect of the present invention, FIG. 1 provides a system 10 having a substrate 12, a conductive layer 14, and an array of free-standing nanowires 16. The array of free-standing nanowires 16 can be grown, or positively planted on the conductive layer 14. If planted, the array of nanowires can be substantially uniformly oriented or randomly oriented, such as like a grouping of fiberglass where a substantial fraction of the nanowires are not affixed directly to the substrate. If grown, one of several methods can be used including chemical vapor deposition (CVD), nanoimprinting, nanotemplating, and/or electrodeposition. Alternatively, other schemes for nanowire growth can be carried out as well. For example, nanowire growth material can be provided by ablating a solid target, such as with a laser. Such a method can be carried out without a substrate, followed by a processes of in situ deposition directly onto a substrate. The nanowires themselves can be conducting or semi-conducting, causing them to experience a net flow of charge into or out of the nanowires when in contact with a control fluid or an analyte-containing fluid. If semi-conducting, various intrinsic doping configurations can be used.

Figure 2:
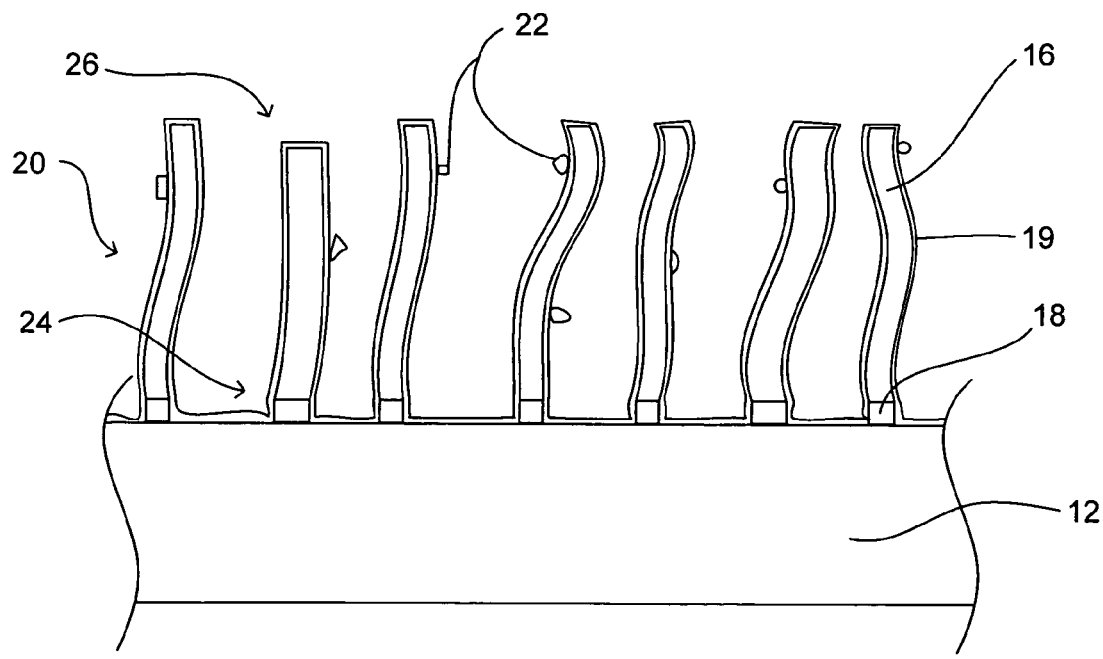
FIG. 2 is a cross-sectional view of an array of free-standing nanowires attached directly to a conductive or semi-conductive substrate, and wherein the nanowires are functionalized with a coating.

Turning to FIG. 2, an enlarged cross-sectional view of a free-standing nanowire sensor is shown. Specifically, system 20 provides a substrate 12 which can be a semi-conductive silicon wafer with or without a silicon oxide surface layer. In this embodiment, the free-standing nanowires 16 are grown from the substrate without an intervening conductive layer. Each free-standing nanowire has a first end 24 and a second end 26. Using a CVD method of growth, the substrate can be decorated with nanoparticles 18 such as gold nanoparticles, titanium silicide alloy nanoparticles, or some other nanoparticle composition that would be expected to allow for nanowire growth. Typically, nanoparticles selected for use can be roughly equi-axial, with finite size less than about 100 nm in all three dimensions. For nanowire growth, a nanoparticle-decorated substrate can be brought to an elevated temperature in the atmosphere of a reactive gas. Under certain conditions, the nanoparticles can be selected to catalyze the gas decomposition. For different nanoparticle and gas combinations, a wide range of conditions can be used. For example, when the nanoparticles used are gold nanoparticles and the gas used is silane ($SiH_4$), the partial pressure and temperature selected for use can be 1 mbar and 450° C. Alternatively, when using silicide nanoparticles, temperatures of about 800° C. can be used. In either case, the nanoparticle can catalyze the decomposition of the gas into volatile components like hydrogen gas, which in turn can desorb. Other components like silicon can further be absorbed or adsorbed by the nanoparticle. Once the nanoparticle becomes saturated by the adsorbed or absorbed material, free-standing nanowires can begin to precipitate or nucleate out of the nanoparticle. A free-standing nanowire can continue growing with a diameter that is related to the size of the nanoparticle catalyst. Changing the growth conditions can stop or alter the nanowire growth.

Once an array of free-standing nanowires 16 are grown or deposited on a substrate, functionalization of the nanowires can be carried out using one of a number of methods. By "functionalization," what is meant includes the various processes in which a nanowire surface can be modified chemically or physically by application of a receptor species that promotes (or suppresses) chemical or electrical interaction with certain analytes or other substances to be tested in an environment. For example, silicon nanowire surfaces can contain native oxide groups, i.e., Si—OH groups. These silicon nanowires can be chemically treated with a surfactant, thus functionalizing the surface. One such surfactant can include an amino silane, wherein upon chemical treatment with such an amino silane surfactant, the silicon surface functional groups of the nanowire can be changed to amine groups. In a more detailed aspect, nanowire surface functionalization can also include the attachment of bio molecules, such as antibodies, to the surface of the nanowire. In another embodiment, functionalization can include the coating of a nanowire surface with an insulating or dielectric material. A functionalization process for chemical treatment of the nanowire surface may be as simple as a room-temperature rinse with a dilute solution of a receptor species, e.g., aqueous amino silanes, followed by a rinse with de-ionized water. In another example, functionalization can include the decoration of the nanowire surface with nanoparticles that can be deposited from solution or from vapor. One embodiment includes the deposition of platinum or palladium nanoparticles that catalyze the dissociative adsorption of hydrogen for its detection.

Functionalization results in a physically or chemically attached coating 19 that can be interactive with an analyte or analyte to be discovered in fluid. Because of the large surface area, individual electrical responses of the grown and sensitized (or functionalized) nanowires can yield a large detection signal. Moreover, by exploiting the collective electrical response of the array, more conventional charge-sensitive or current-sensitive measurement methods can be used. This can enable the production of commercial products based on traditional detection circuitry.

Many physical or chemical coating substances can be used as a receptor and/or for various other purposes. For example, coating 19 can be a composition that is reactive with a specific analyte 22 wherein, upon reaction, a charge transfer occurs that can be sensed electrically. Alternatively, coating 19 can be a dielectric layer that has been added to the surface of the nanowire 16 such that an altered free charge will attract or attach to an analyte 22. For example, as an analyte gets stuck to the surface of the dielectric layer, an unbalanced charge will induce a counter charge in the nanowire and form a nano-parallel plate capacitor. In other words, each nanowire of the nanowire array could act individually as a capacitor. Similarly as set forth above, a counter charge in the nanowire that is displaced can produce a microscopic or nanoscopic current in each nanowire that can be detected. In embodiments where electrical charge is lured into or out of the surface, since the counter charge will deplete the density of free carriers in the nanowire (such as through doping) the impedance of the nanowire(s) can be modified. The electrical state of the nanowire(s) is thus indicative of its surface state and can be monitored in the nanowire array via measurement of the resistance, the capacitance, or even the complex impedance at a predetermined frequency. If the nanowires are probed using a transient signal (voltage or current) a difference between an array of unmodified nanowires compared to an array of nanowires with depleted charge densities can be measured. In this embodiment, it is assumed that the energy necessary to cause electromagnetic fields to polarize a substance is different than the energy necessary to cause electromagnetic fields to propagate through free space. This is because energy is required to move electrons and ions. If one nanowire has charged species adsorbed near its surface and these charges have polarized centers, an electron can find a lower energy state than by propagation through a lattice. Thus, the electron can essentially be trapped and the conductivity of the nanowire will decrease. Such a trap is a function of the material properties of the nanowire, and the state of charge or polarization of the sensed molecule.

In a further detailed aspect, a nanowire can be configured, either by functionalization or by its inherent properties, such that a charge present in the nanowire can be lured to or out of the nanowire surface by chemical attraction to a polar molecule that may be present in a fluid as an analyte. A free-standing array of nanowires, such as in a sensor of the present invention, can comprise multiple free-standing nanowires having a specific chemical affinity. Some compounds will be attracted to the surface while others will be repelled. This is the nature of chemical bonding. The attraction process essentially changes the distribution function of local electron probabilities. This change in distribution function can change the total probability of electrons in the nanowire. The capacitance of a device is in effect a measure of the total electron concentration in that region compared to some other region. More electron mobility results in more capacitance. Because of the large volume of nanowires as well as the large surface area provided by the nanowires, measurements of capacitance by perturbing the equilibrium state with a small fluctuating voltage and observing the displacement current can be realized. Such a change will reflect the presence and extent of chemically attached additional molecules. The molecules are the materials that are being detected.

In one example of this phenomenon, upon exposure to a solution or gas sample, if a predetermined analyte is present that can contact the nanowire, a decoupling or charge alteration of the system will cause the charge at the surface of the nanowire to find ground through the molecule and nanowire. The charges present can then use the nanowire as conduits to a ground plane, thus producing from nanoscopic to microscopic currents that. are detectable. To illustrate, in one embodiment, a nanowire array could be used to detect the presence of methanol. As methanol includes a polar —OH group, as the —OH group approaches or contacts the nanowire, the hydrogen provides a slightly positive charge (as the hydrogen is electron deficient in the —OH group) to the surface of the nanowire. This new net charge at or near the surface of the nanowire would alter the electron charge present in the nanowire, thus providing a detectable charge transfer. Such sensitivity is not available using standard sized wires.

Figure 3:
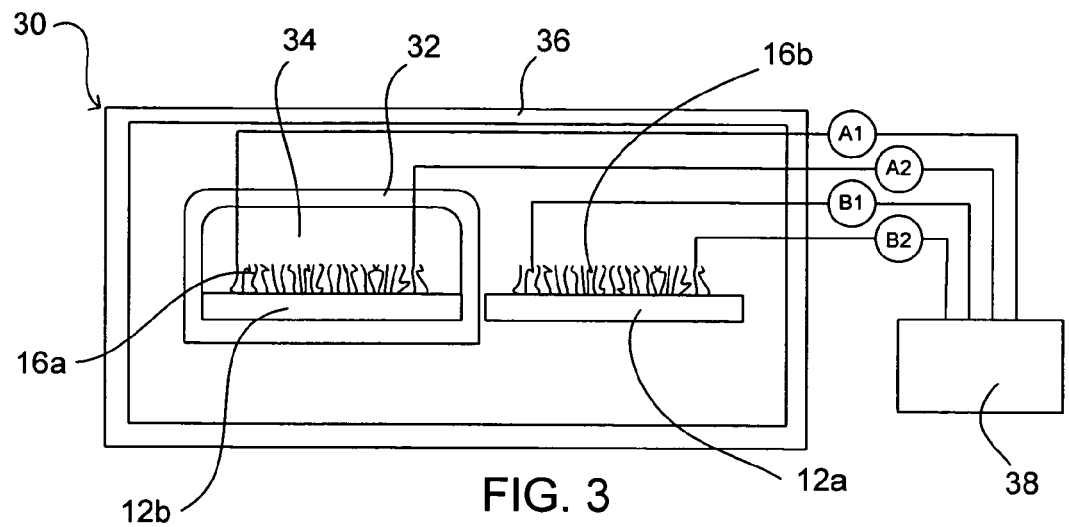
FIG. 3 is free-standing nanowire conductive comparison system in accordance with an embodiment of the present invention.

Turning to FIG. 3, in one embodiment, differential measurements of conductance can be carried out using system 30. Upon conductive or semi-conductive substrates 12a, 12b is grown or deposited two nanowire array samples 16a, 16b. The nanowire array samples 16a, 16b can be coated or uncoated, depending on the embodiment. Nanowire array sample 16a is substantially sealed or enclosed by walls 32 that define a chamber 34. Within the chamber can be an inert gas or a simple gas atmosphere, e.g., nitrogen. Nanowire array sample 16b can exposed to the surrounding atmosphere. In the embodiment shown, nanowire array sample 16b is completely open to the atmosphere of the system, but is within an outer shell 36. Alternatively, nanowire array sample 16b can be within a chamber similar to chamber 34 with the proviso that such a chamber be configured with inlets and/or outlets to allow air, water, or other fluids from the environment being sampled to flow through the device. In the embodiment shown, because the differential measurements to be made can be nanoscopic, in one embodiment, outer shell 36 can be present that electrically and environmentally shields the sensor components from external environmental or electrical forces.

Elements A1, A2, B1, and B2 provide electrical contact points on both the nanowire array samples 16a, 16b. However, each contact point can actually be at two nanowire locations, if one wants to utilize a "4-point probe" measurement. Information provided by Elements A1, A2, B1, and B2 is relayed electrically to a chip or computer 38 that is human- or machine-readable. In the embodiment shown, one nanowire at each spot is used for measuring voltages or other electrical properties by forcing a current between ends of each sample. For example, current flow between element A1 and A2 can be compared to current flow between element B1 and B2. The measurement can occur as one nanowire (or a set of nanowires) are electrically connected to another nanowire (or set of nanowires at a distal end). There may or may not be a perfect separation between the sets of nanowires, as such perfect comparable separation is not important if one is looking for changes in the surface conductivity due to environmental effects. In further detail, this embodiment provides the ability to take a measurement of conduction through the array of nanowires during exposure and recovery from an invasive chemical or biological compound.

Figure 4:
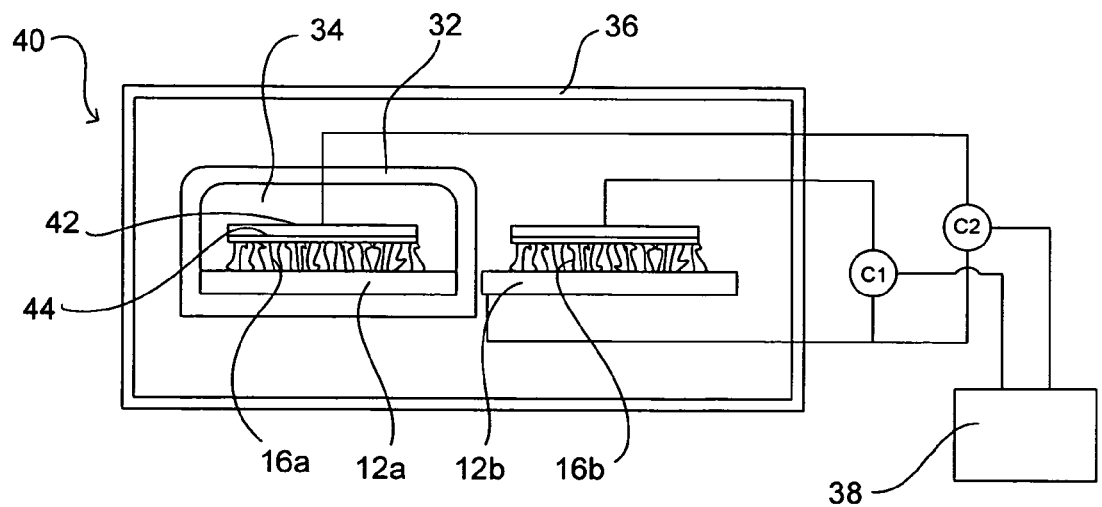
FIG. 4 is a free-standing nanowire capacitive comparison system in accordance with an embodiment of the present invention.

Referring to FIG. 4, in one embodiment, differential measurements of capacitance can be carried out using system 40. Specifically, one can consider the differential capacitance between an unprotected device and a protected or substantially sealed device by changes in the ambient. In this embodiment, upon conductive or semi-conductive substrates 12a, 12b is grown or deposited two nanowire array samples 16a, 16b. The nanowire arrays 16a, 16b can be coated or uncoated, depending on the embodiment. Nanowire array sample 16a is substantially sealed or enclosed by walls 32 that define a chamber 34. Nanowire array sample 16b is exposed to the surrounding atmosphere. Capacitance measurement points C1, C2 are present to measure current to or from the array of nanowires (to or from the counter-capacitive plate 42). The counter-capacitive plate 42 can be a stainless steel porous frit in one embodiment. Though not required, a porous plate is used such that gasses and/or liquids can pass freely therethrough for contact with the nanowire surfaces. To avoid direct contact between the stainless steel frit and the surface of the nanowires, a thin insulating film 44 is placed therebetween. The film can be porous to allow liquids and/or gases through. Examples of films include Nucleopore® membranes or other membranes known by those skilled in the art. Alternatively, rather than using an insulating film, the surface of the nanowires can be coated as shown in FIG. 2 to prevent contact between the nanowires and the counter-capacitive plate.

In one embodiment, a measurement that can be taken is to determine whether an analyte has adhered to a one or more nanowires of the array of nanowires, and if the analyte has an inherent dipole. To accomplish this, capacitive measurement points C1, C2 are measured as a function of changes in the frequency of measurement (ionic bound materials will diffuse given adequate field intensity).

Figure 5:
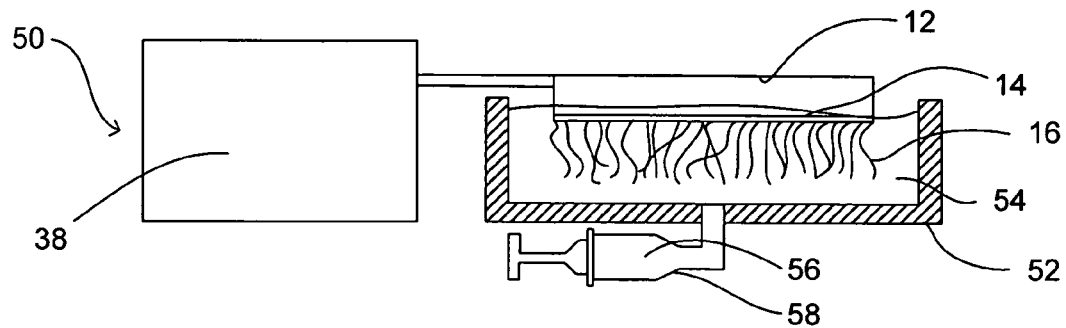
FIG. 5 is a free-standing nanowire conductive system in accordance with an embodiment of the present invention.

Referring now to FIG. 5, a simple embodiment is shown as system 50. Specifically, a substrate 12 having an array of free-standing nanowires 16 is shown. The base of each free-standing nanowire is in electrical communication with adjacent free-standing nanowires via a conductive layer 14. A control or comparative free-standing nanowire array sensor is not present in this embodiment. A fluid container 52 containing a fluid 54 that does not substantially interact with the nanowires is present. Electrical conductance information can then be collected by the nanowires and electrically transferred to a computer, chip, or other signal measurement device 38 that provides machine- or human-readable information. After obtaining a base-line reading of the fluid 54, a second fluid 56 (which is suspected of containing an analye) can be introduced to fluid 54 using a pump 58 or other similar device, and a change in electrical conductance can be compared to the base-line reading. Such an arrangement can provide quantitative or qualitative information, depending on the configuration and/or sensitivity of the system. The nanowires can either be in their sensitive native state, or can be functionalized to be reactive, interactive, or insulating with respect to a predetermined analyte. In one embodiment, the second fluid can be pre-processed to remove any contaminants that may interfere with the reading, e.g., membrane filtration, etc.

Figure 6:
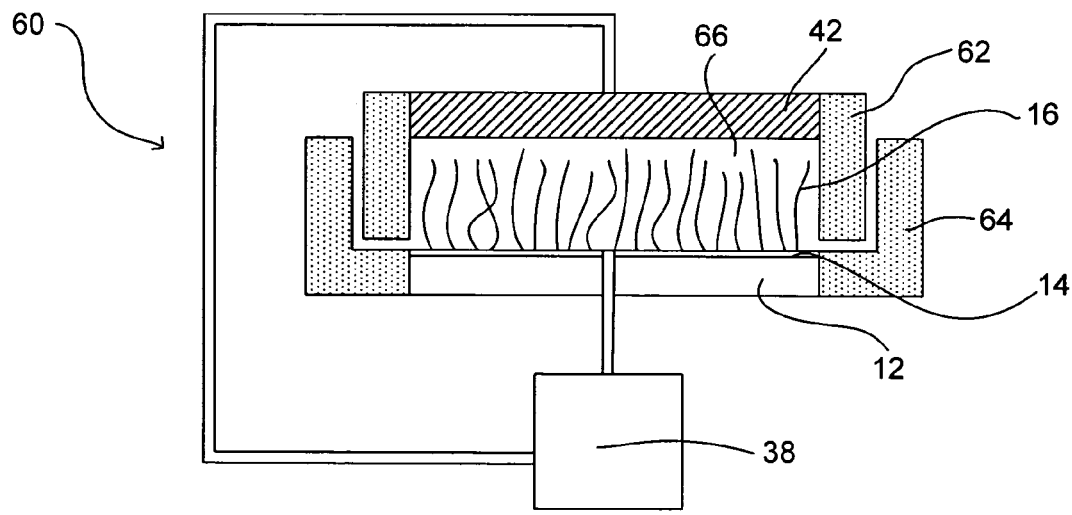
FIG. 6 is a free-standing nanowire capacitive system in accordance with an embodiment of the present invention.

FIG. 6 provides yet another example, wherein system 60 includes a substrate 12 and an array of free-standing nanowires 16 electrically coupled to one another at or near the base of each individual nanowire. A conductive layer 14, such as a thin metal coating, is present to provide such electrical communication between individual free-standing nanowires, though such a layer is not strictly required. For example, in some embodiments, electrical communication between nanowires can be provided by the substrate itself, e.g., semiconducting substrate such as silicon. Also present, opposite the array of nanowires 16, is a counter-capacitive plate 42. This plate can be of any conductive material that is functional, or can be a second free-standing nanowire array. If the counter-capacitive plate 42 comprises free-standing nanowires as well, two sensors can be placed opposing one another and the chemical or biological substance can be placed between the sensor surfaces. This can double the effective capacitance of the system. Further, this can double the change in the displacement current caused by the impingement of a material to study.

Unlike the sensor shown in FIG. 4, the space between the free-standing nanowires 16 and the counter-capacitive plate 42 is not provided by an insulating film, but is provided by insulating spacers 62, 64 that are configured such that when they are mated, the free-standing nanowires 16 do not substantially contact the counter-capacitive plate. In this configuration, once the free-standing nanowires have been spent, or if a different application is desired, the structure comprising the nanowires, i.e., insulator 64, substrate 12, conductive film 14, and free-standing nanowires 16, can be removed and replaced. Electrical capacitance information across the gap 66 can then be collected by the system and electrically transferred to a computer or chip 38 that provides machine- or human-readable information. In this embodiment, computer 38 provides the dual function of providing current to the system (thereby acting as a power source) as well as receiving electrical information from the capacitive system.

Figure 7:
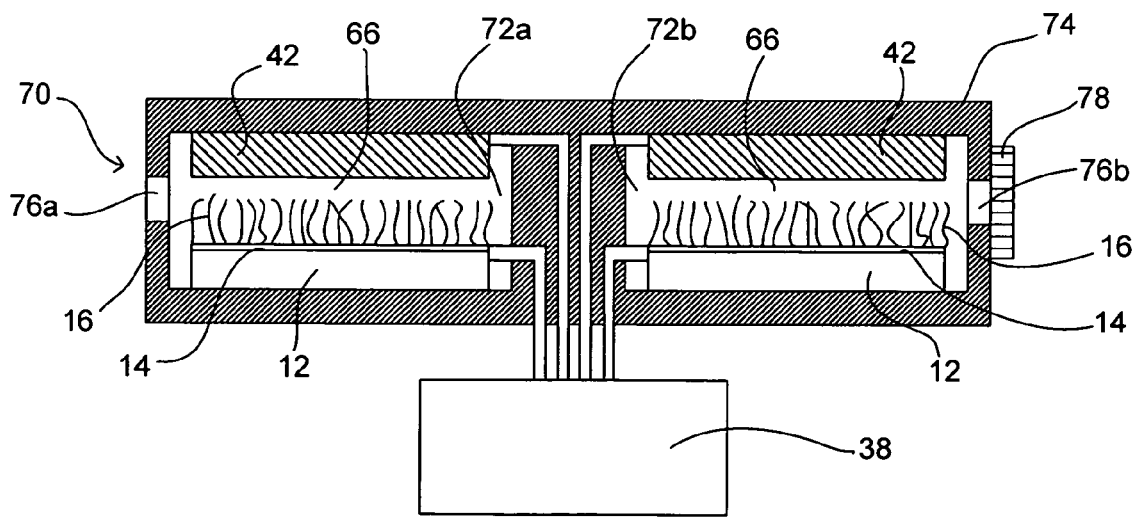
FIG. 7 is a free-standing nanowire capacitive comparison system having a membrane selective inlet port in accordance with an embodiment of the present invention.

Turning now to FIG. 7, an alternative embodiment similar to FIG. 4 is provided as system 70 wherein two substantially similar chambers 72a, 72b are defined by a housing 74. Each chamber 72a, 72b comprises a substrate 12, a conductive film 14, and an array of free-standing nanowires 16 of similar density (with individual nanowires of similar length and diameter). Across gaps 66 from the nanowires 16 are counter-capacitive plates 42. To chamber 72a can be added a fluid through port 76a. To chamber 72b can be added a fluid through port 76b. Thus, two fluids can be simultaneously tested for capacitance properties at the same time in nearly identical chambers (the difference being the non-exact array of nanowires, though their conductance and capacitive properties can be approximately the same). Using this structure, a first fluid that is used as a control can be added to chamber 72a, while a second fluid that may contain an analyte can be added to chamber 72b. Computer or chip 38 provides current to the capacitive system, and also receives electrical capacitance information transmitted across gaps 66. By carrying out a comparison of capacitance and/or conductance, the presence and/or quantity of an analyte can be verified or discovered.

Also shown is an optional membrane or filter 78. The membrane can be configured as shown, or in conjunction with the other embodiments of the present invention. In this embodiment, two sensors are configured such that one is separated from the surrounding environment by a filter 78 that excludes only an analyte of interest. By this configuration, a comparison of the differential capacitance between the two sensors can verify the presence of the analyte in the solution. Alternatively, two sensors can be configured such that a filter is provided wherein only a specific ion or ion set to migrate through filter. Thus, only the specific ion or ion set reaches the nanowire for measurement. In one embodiment, the presence of the ion or ion set can complete an electrochemical cell which creates a voltage differential between the outer surface of the system and the center of the nanowire. The addition of an external variable field can then be provided to change the diffusion process depending on the concentration gradient of the coating material used. This arrangement, in essence, provides a concentration measurement tool as one observes the current (or voltage) as a function of the voltage (or current) applied.

The above embodiments can be summarized and expanded upon according to the following observations. First, observations of the change in dielectric constant in and around nanowires based on the adsorption of analytes can provide a polarization effect that can be measured. Observations of the change in dielectric constant in and around nanowires based on the fact that a change from a lack of material coating the nanowires to a material that selectively coats it based on some steric (and/or Van-der-Waals attraction) process can also be measured. Differential Capacitance and conductance measurements between assemblies of nanowires (some able to be exposed and others able to be protected from an environment) can provide electrical information that can be used of qualitative or quantitative analysis.

In addition to that described in the context of. FIGS. 1-7, the following examples are provided to illustrate variations that can be carried out in accordance with embodiments of the present invention, but should not be considered limiting.

In one embodiment, a standalone free-standing nanowire sensor can be used to sense a specific analyte. For example, a palladium (Pd) nanowire can be used to respond to hydrogen gas. Upon application of a small voltage to a free-standing nanowire sensor of the present invention, and upon exposure to hydrogen gas, the free-standing nanowires will swell up to three percent in size. When the gas is removed, the nanowires will shrink to their regular size, leaving atomic gaps or breaks in the individual nanowires, making them non-conductive. By reintroducing hydrogen, the nanowires can swell again, sealing the breaks. As the breaks become sealed, conductance increases which can be measured. As such, measurements of the percentage of hydrogen in an environment can be determined by measuring the amount of current found in the system.

In another embodiment, the nanowire-modified substrate can be one plate of a parallel plate capacitor. If the nanowires are functionalized or activated by chemically binding receptor species, the receptor sites can bind to a particular environmental substance that one wishes to test for. For example, if the detection of lead is desired, a particular type of molecule, virus, or bacterial organism that interacts with lead can be used. Upon interaction with the lead, the electrical properties can be detected as they are changed. When a second, counterelectrode plate is used, the two plates can be oriented such that the nanowires are between the plates.

To provide further detail regarding an embodiment of the present invention, one can consider a silicon nanowire with a radius of 10 nm and a length of 100 nm. The volume of such a nanowire is $7.9 \times 10^{-18}$ cm$^3$ and the surface area is $3.14 \times 10^{-11}$ cm$^2$, which corresponds to about $25 \times 10^3$ surface Si atoms. If a single carrier is present in a nanowire, the equivalent carrier density is $1.3 \times 10^{17}$ carriers/cm$^3$. Now consider that such a nanowire is covered with a 2 nm thick layer of an electronic grade silicon dioxide. Such a silicon-oxide interface will have a surface state density of about $10^{10}$/cm$^2$, which means that, on average, each nanowire will have 0.3 surface states (or that each nanowire will most likely have none or one surface states).

In the above-described embodiments, and other similar embodiments, the system can include a computer, chip, or other measurement apparatus that can be inserted into a simple device for rapid analysis in the field. Depending on the nature of the investigation, data may then be stored for later analysis by a more capable instrument in a laboratory setting, or can be analyzed using an on-site computer, such as a handheld computer. Analyses may involve both impedance spectroscopy and also a variety of optical spectroscopies. Such a device can make a frequency-dependent impedance measurement or a simple optical measurement that will indicate the presence and approximate quantity of a species of interest. Alternatively, a desk top or laptop can be configured to perform more exhaustive and quantitative analysis of the coupons, using both electrical and optical characterization.

The present invention provides a means for which one can take all of the known sensor effects of materials and consider the effect of using a nanodevice as the interrogator. For example, alcohols by their nature tend to adhere nicely to many surfaces. This is due to the fact that they contain a polar group and a non-polar group. The strength of absorption is a function of the configuration of the molecule compared to the surface upon which it is adsorbing. Thus, the effect of a series of alcohols on the capacitance and conductance of an array of free-standing nanowires of various compositions would be easily ascertainable.

It is to be understood that the above-referenced arrangements are only illustrative of the application for the principles of the present invention. Numerous modifications and alternative arrangements can be devised without departing from the spirit and scope of the present invention. While the present invention has been shown in the drawings and fully described above with particularity and detail in connection with what is presently deemed to be the most practical and preferred embodiment(s) of the invention, it will be apparent to those of ordinary skill in the art that numerous modifications can be made without departing from the principles and concepts of the invention as set forth in the claims.

What is claimed is:

1. A method of detecting the presence of an analyte in a test fluid environment, comprising:
   providing a first array of free-standing nanowires that is interactive with an analyte, said first array of free-standing nanowires having individual nanowires that are electrically interactive with one another, said first array of free-standing nanowires being electrically coupled to a chip or computer that is human- or machine-readable;
   exposing the first array of free-standing nanowires to a test fluid environment suspected of containing the analyte;
   measuring an electrical property provided by the first array of free-standing nanowires upon exposure to the test fluid environment.

2. A method as in claim 1, further comprising the steps of providing a second array of free-standing nanowires, said second array of free-standing nanowires having individual nanowires that are electrically interactive with one another, said second array of free-standing nanowires being electrically coupled to the chip or computer;
   exposing the second array of free-standing nanowires to a control fluid environment;
   comparing the electrical property provided by the second array of free-standing nanowires upon exposure a control fluid environment to the electrical property provided by the first array of free-standing nanowires, thereby providing a differential measurement.

3. A method as in claim 2, wherein the second array of free-standing nanowires is also configured to be interactive with the analyte, and wherein the control fluid environment is known to be void of the analyte, or is known to have a fixed concentration of the analyte, thereby providing a basis for the comparing step.

4. A method as in claim 2, wherein the second array of free-standing nanowires is configured to be non-interactive with the analyte, and wherein the control fluid environment and fluid environment are substantially the same fluid composition, thereby providing a basis for the comparing step.

5. A method as in claim 2, wherein the first array of free-standing nanowires is functionalized with a composition interactive with the analyte.

6. A method as in claim 2, wherein the first array of free-standing nanowires is functionalized with an insulating composition.

7. A method as in claim 2, wherein the electrical property of the array of free-standing nanowires is conductance or impedance at a predetermined frequency.

8. A method as in claim 6, wherein the electrical property between the analyte and at least one individual free-standing nanowires is capacitance or impedance at a predetermined frequency.

9. A method of detecting the presence of an analyte in a fluid environment, comprising:
   providing a detecting system comprising a first capacitive plate having a first array of free-standing nanowires that is interactive with an analyte, said first array of free-standing nanowires comprising individual nanowires that are electrically interactive with one another, and a second capacitive plate positioned in proximity to the first capacitive plate such electrical communication between the first capacitive plate and the second capacitive plate occurs in the presence of the test fluid environment,
   placing the test fluid environment in continuous contact with the first capacitive plate and the second capacitive plate;
   applying electrical current to at least one of the first capacitive plate and the second capacitive plate; and
   measuring an electrical property passed capacitively between the first capacitive plate and the second capacitive plate.

10. A method as in claim 9, further comprising the steps of:
    providing a control system comprising a third capacitive plate and a fourth capacitive plate that are substantially configured the same as the first capacitive plate and the second capacitive plate, respectively, and
    placing a control fluid that is known to be void of the analyte in continuous contact with third capacitive plate and the fourth capacitive plate, thereby providing a comparison basis for the measuring step.

11. A method as in claim 9, further comprising the step of:
    providing a control system having a third capacitive plate and a fourth capacitive plate that are substantially configured the same as the first capacitive plate and the second capacitive plate, respectively, except that the nanowires of the third and fourth capacitive plates are not interactive with the analyte, and
    placing the test fluid in contact with the control system, thereby providing a comparison basis for the measuring step.

* * * * *